United States Patent
Shen et al.

(10) Patent No.: US 8,988,085 B2
(45) Date of Patent: Mar. 24, 2015

(54) SENSOR FOR MEASURING THE CONCENTRATION OF A SOLVENT OR SOLUTE IN A MIXED SOLUTION SYSTEM

(75) Inventors: Jun Shen, Vancouver (CA); Caikang (Elton) Gu, Burnaby (CA); Jiujun Zhang, Richmond (CA); David P. Wilkinson, North Vancouver (CA); Haijiang Wang, Burnaby (CA)

(73) Assignee: National Research Council of Canada, Ottawa (CA)

( * ) Notice: Subject to any disclaimer, the term of this patent is extended or adjusted under 35 U.S.C. 154(b) by 515 days.

(21) Appl. No.: 13/147,025

(22) PCT Filed: Feb. 5, 2010

(86) PCT No.: PCT/CA2010/000160
§ 371 (c)(1),
(2), (4) Date: Jul. 29, 2011

(87) PCT Pub. No.: WO2010/088770
PCT Pub. Date: Aug. 12, 2010

(65) Prior Publication Data
US 2011/0291676 A1    Dec. 1, 2011

Related U.S. Application Data

(60) Provisional application No. 61/202,209, filed on Feb. 5, 2009.

(51) Int. Cl.
*G01N 27/22* (2006.01)
(52) U.S. Cl.
CPC .................................... *G01N 27/22* (2013.01)
USPC ....................................................... 324/679

(58) Field of Classification Search
USPC ....................................................... 324/679
See application file for complete search history.

(56) References Cited

U.S. PATENT DOCUMENTS

| 4,435,267 A | 3/1984 | Batzold et al. |
| 4,939,467 A | 7/1990 | Nogami et al. |
| 5,196,801 A | 3/1993 | Nogami et al. |

(Continued)

FOREIGN PATENT DOCUMENTS

| CA | 1259374 | 9/1989 |
| CA | 2251874 | 10/1997 |

(Continued)

*Primary Examiner* — Jeff Natalini
(74) *Attorney, Agent, or Firm* — Catherine Lemay

(57) ABSTRACT

The invention described relates to an apparatus and method for measuring the concentration of a low molecular weight alcohol, in an aqueous liquid feed solution, comprising a first sensor including a hydrophilic capillary tube having an inner diameter, being disposed between two electrodes to form a first capacitor, a second sensor including a hydrophobic capillary tube having the same inner diameter as a capillary tube of the first sensor; said hydrophobic capillary tube having a hydrophobic coating on the inner diameter, being disposed between two electrodes to form a second capacitor, wherein the first hydrophilic and second hydrophobic sensors are dipped to the same depth in the aqueous solution to measure the solution concentration, means for measuring the capacitance of the two capacitors, and control means including a control circuit driven by a computer, wherein the difference in capacitance between the two capacitors is a measure of the concentration of the solution, independent of the depth of dipping of the two capacitors in the aqueous solution. In another embodiment, a single hydrophilic sensor is employed.

19 Claims, 13 Drawing Sheets

Structure of the sensor

(56) References Cited

U.S. PATENT DOCUMENTS

| | | | |
|---|---|---|---|
| 5,424,799 A * | 6/1995 | Nakamura et al. | 396/626 |
| 5,545,303 A | 8/1996 | Schasfoort et al. | |
| 6,443,111 B1 * | 9/2002 | LaDow | 123/90.11 |
| 6,566,892 B2 * | 5/2003 | Schaefer et al. | 324/663 |
| 6,748,793 B2 | 6/2004 | Rabinovich et al. | |
| 6,815,682 B2 | 11/2004 | Rabinovich et al. | |
| 7,560,865 B2 * | 7/2009 | Katou et al. | 313/625 |
| 2002/0008522 A1 | 1/2002 | Schnell et al. | |
| 2002/0109511 A1 | 8/2002 | Frank | |
| 2002/0170824 A1 * | 11/2002 | Frerichs | 204/416 |
| 2003/0033858 A1 * | 2/2003 | Lambert et al. | 73/53.01 |
| 2008/0029622 A1 * | 2/2008 | Pommersheim | 239/424 |
| 2008/0262740 A1 * | 10/2008 | Potter | 702/19 |

FOREIGN PATENT DOCUMENTS

| | | |
|---|---|---|
| EP | 1275732 | 1/2003 |
| JP | 2257052 | 10/1990 |

* cited by examiner

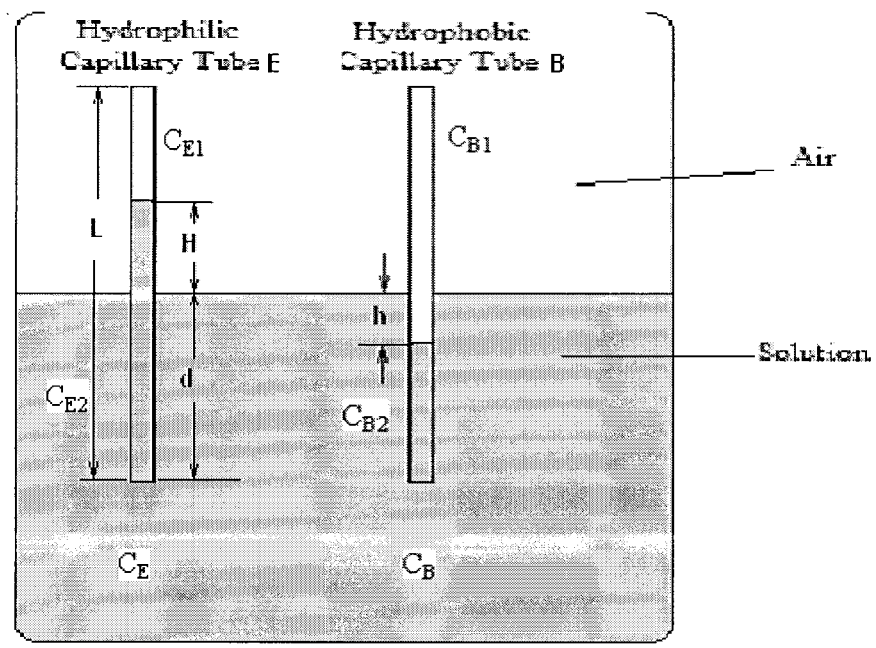
Fig.1. Hydrophilic and hydrophobic capillary tubes.
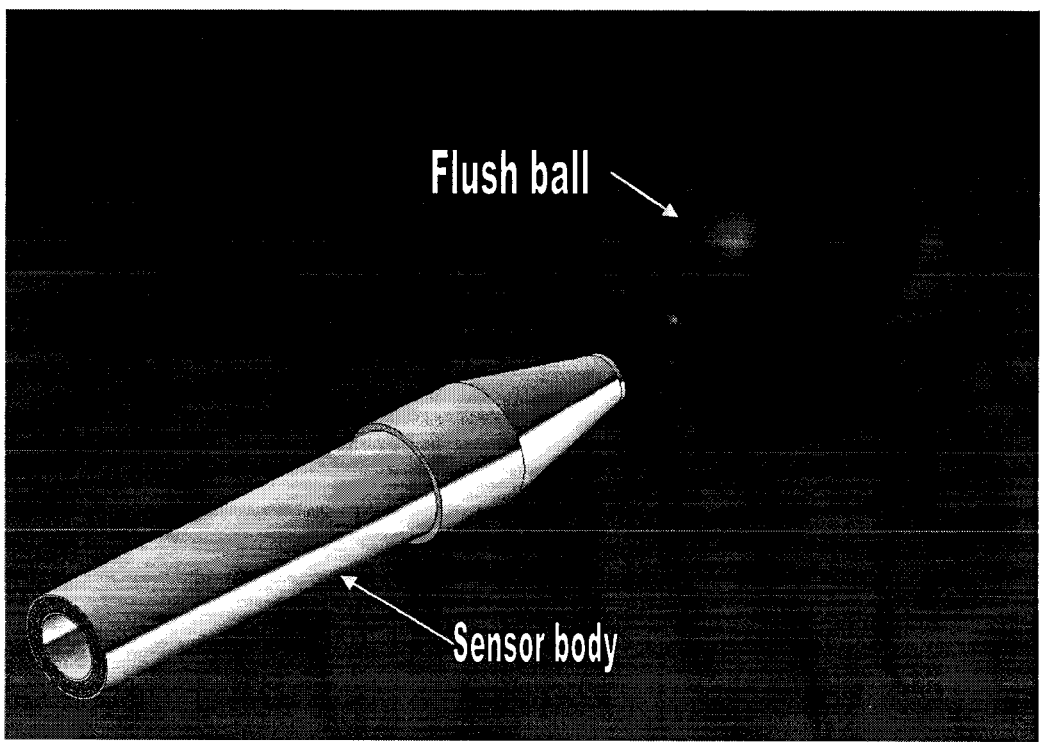
Fig. 2. Outlook of the sensor

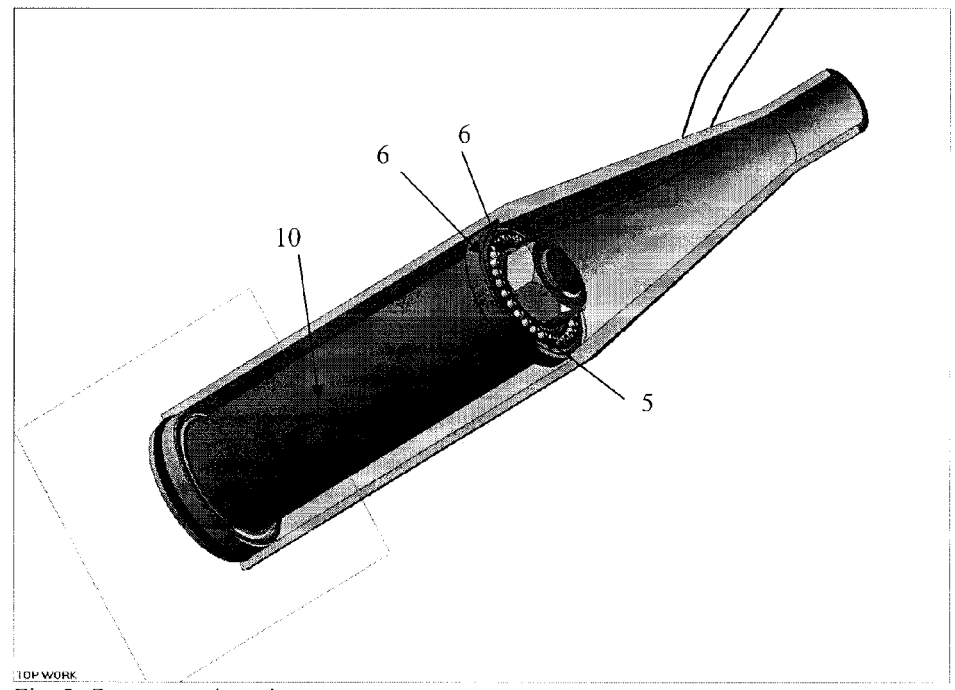
Fig. 3. Sensor section view
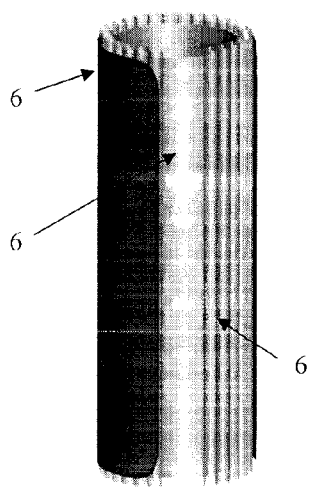
Fig. 4. The sensing parts of the capillary methanol/ethanol sensor

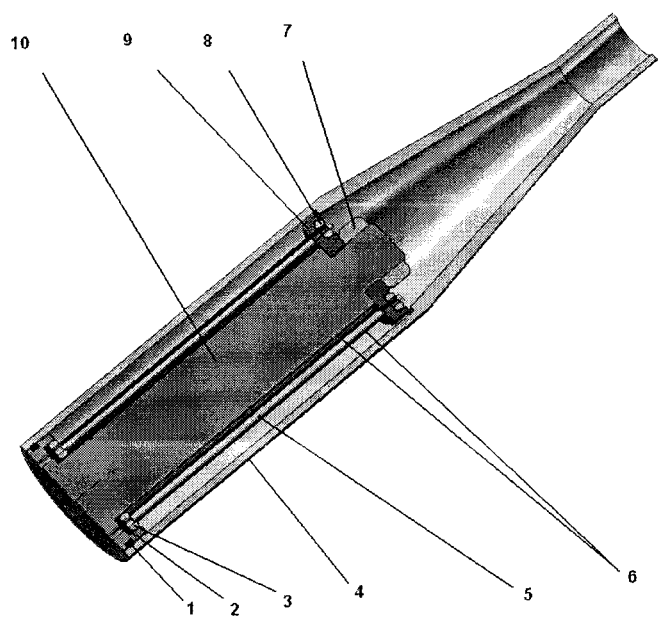
Fig 5. Structure of the sensor

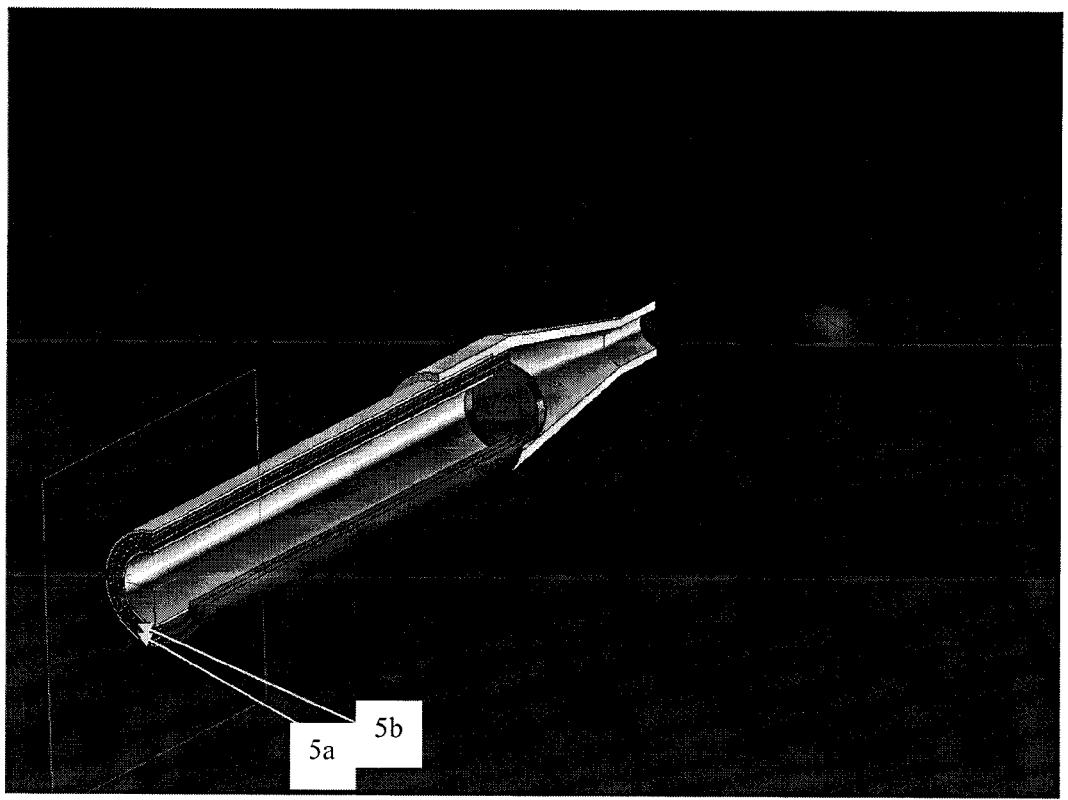
Fig. 6. Coaxial methanol/ethanol sensor

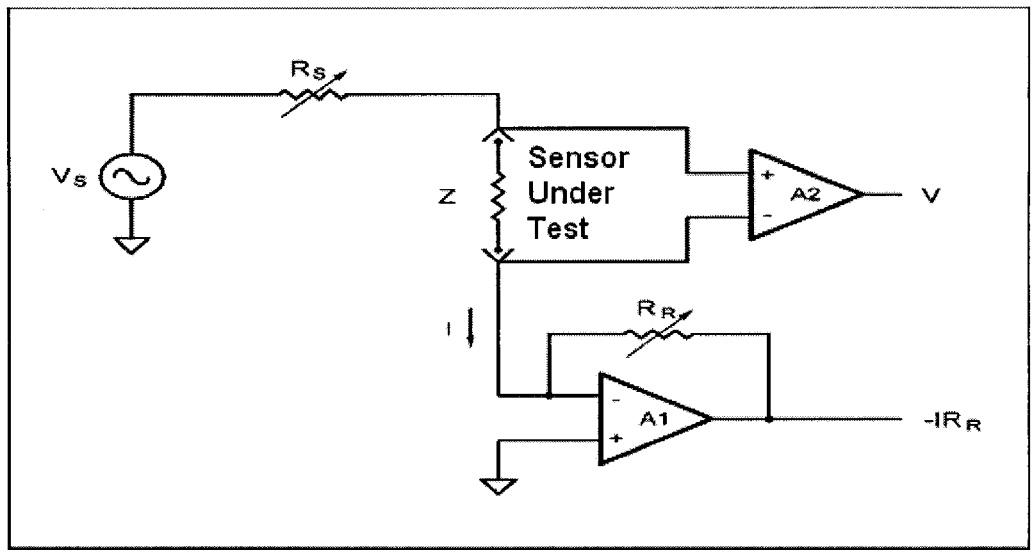
Fig. 7 Capacitance measurement of the sensor
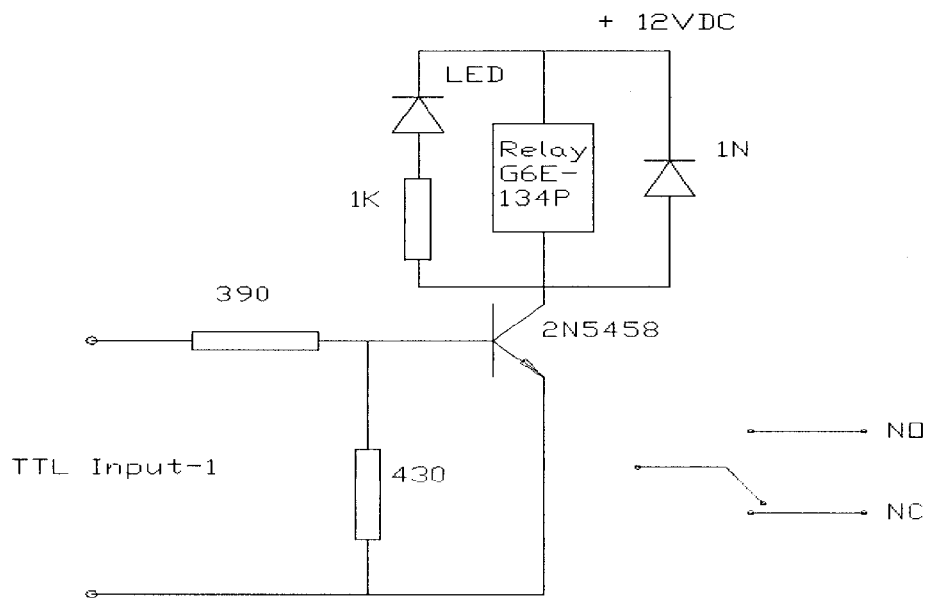
Fig. 8 Computer controlled capacitance measurement control circuit

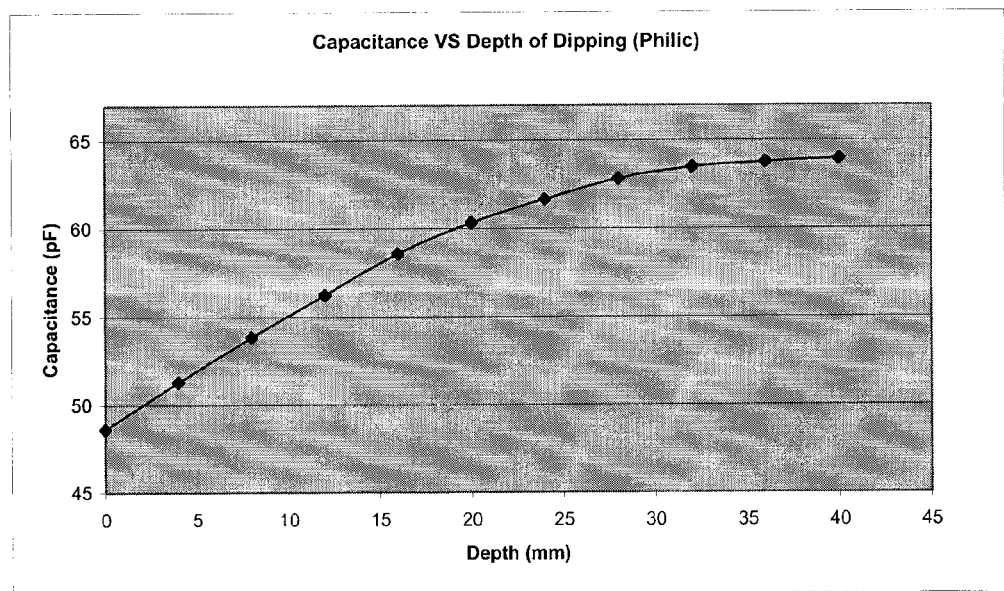
Fig. 9. Hydrophilic linearity performance
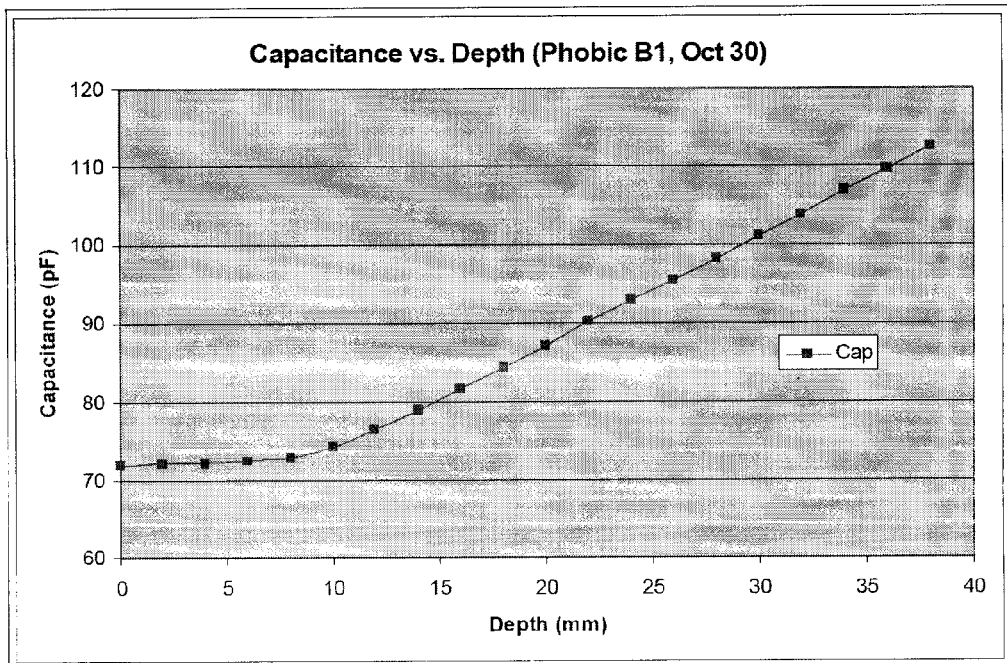
Fig. 10. Hydrophobic linearity performance

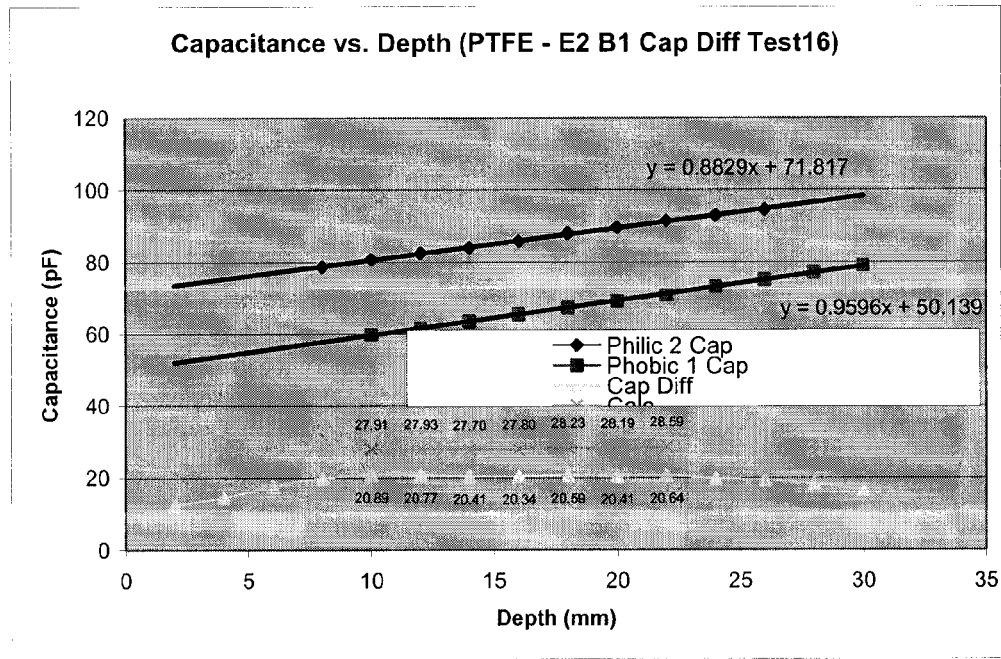
Fig. 11 Sensor accuracy test
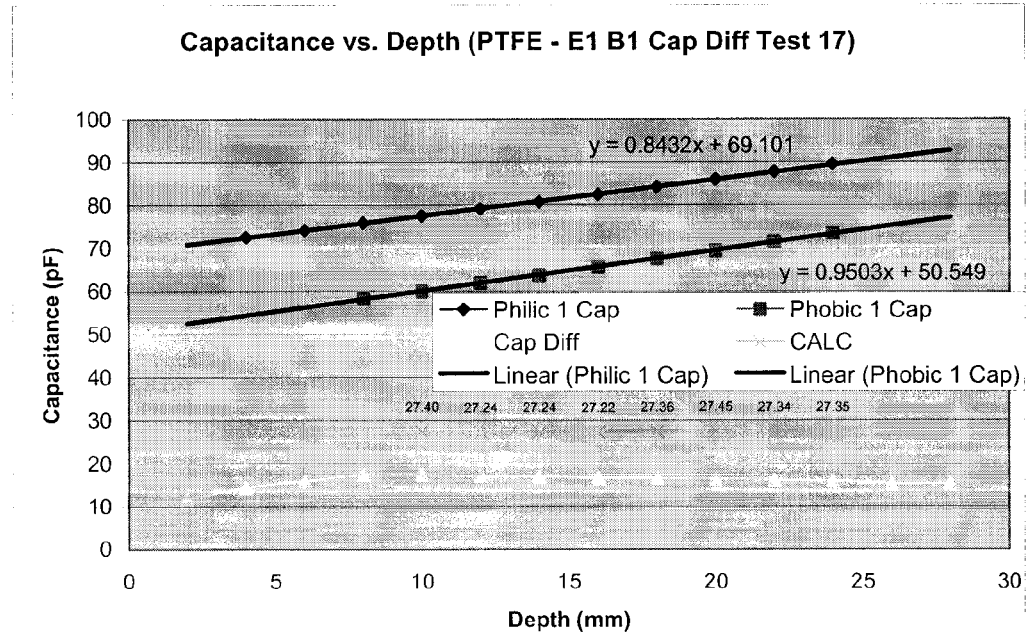
Fig. 12 Sensor accuracy test

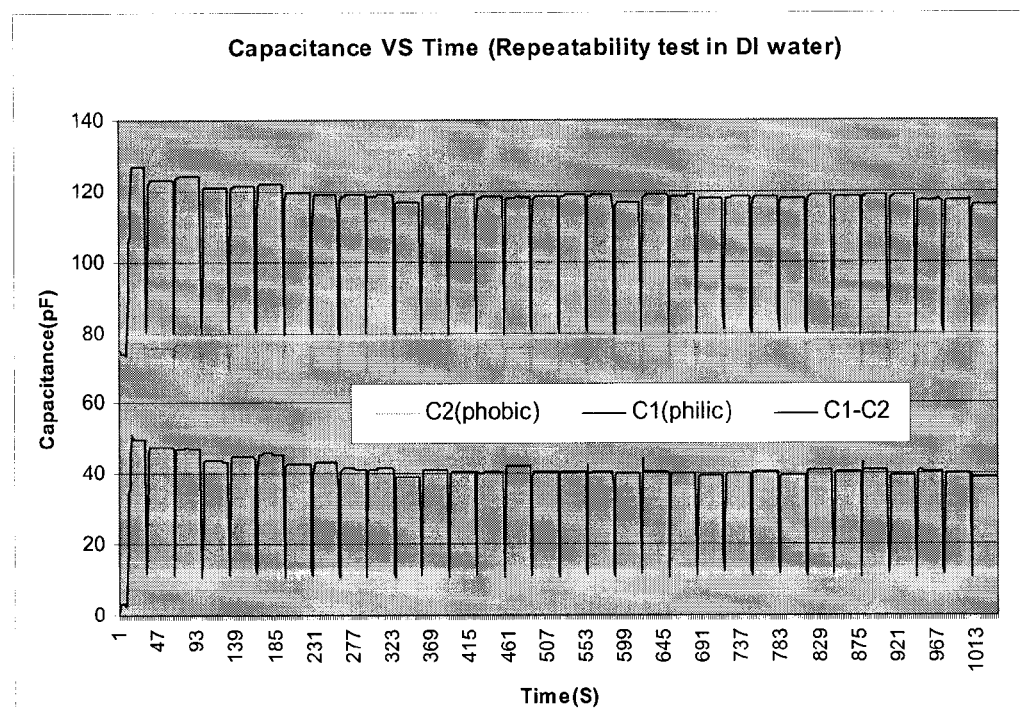
Fig. 13 Sensor repeatability test at same depth of dipping
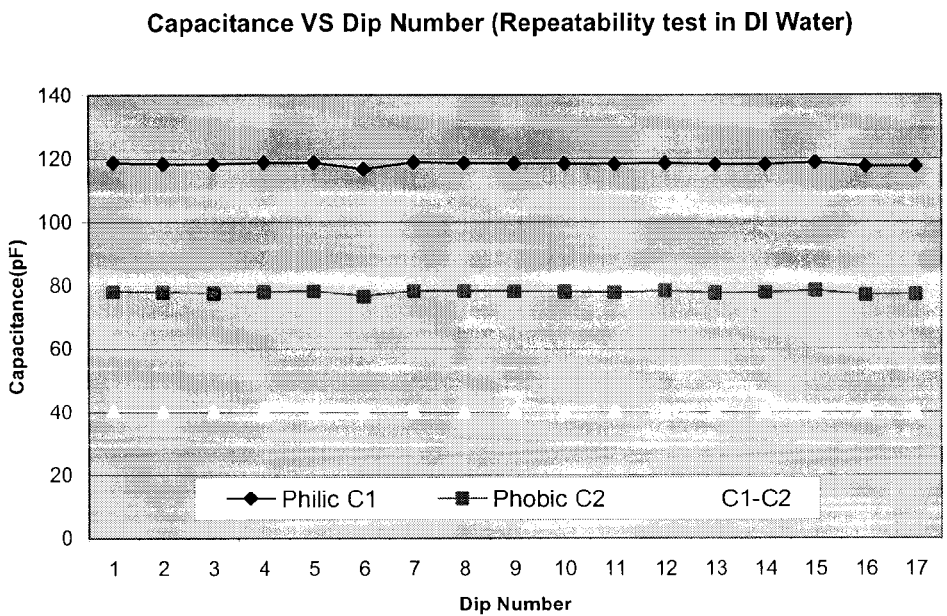
Fig. 14 Sensor repeatability test at different depth of dipping

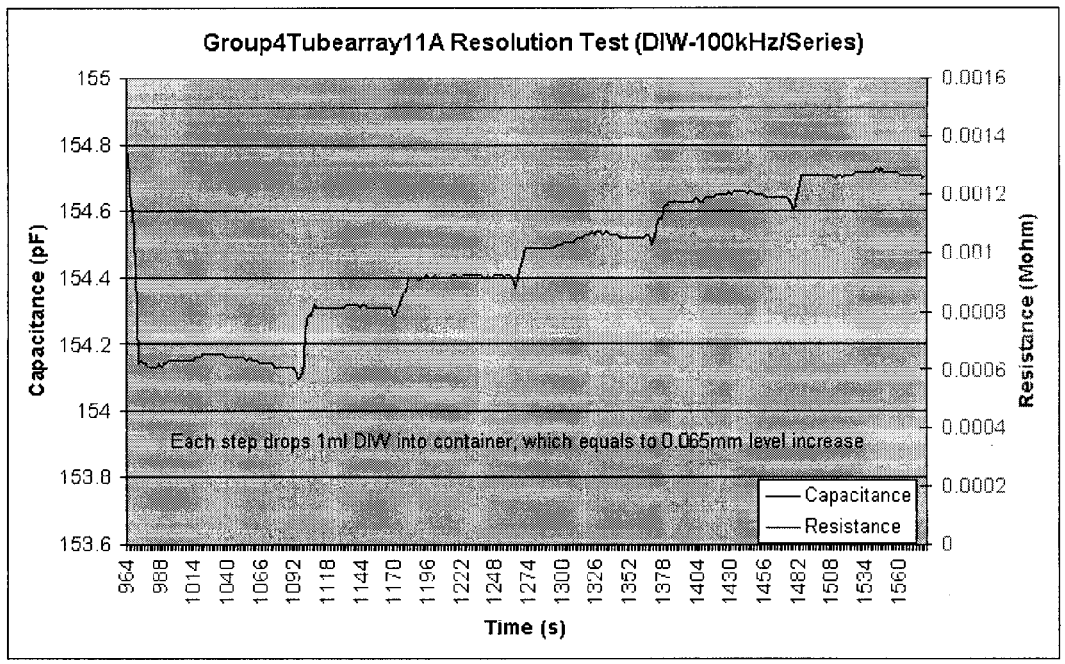
Fig. 15 Sensor resolution test
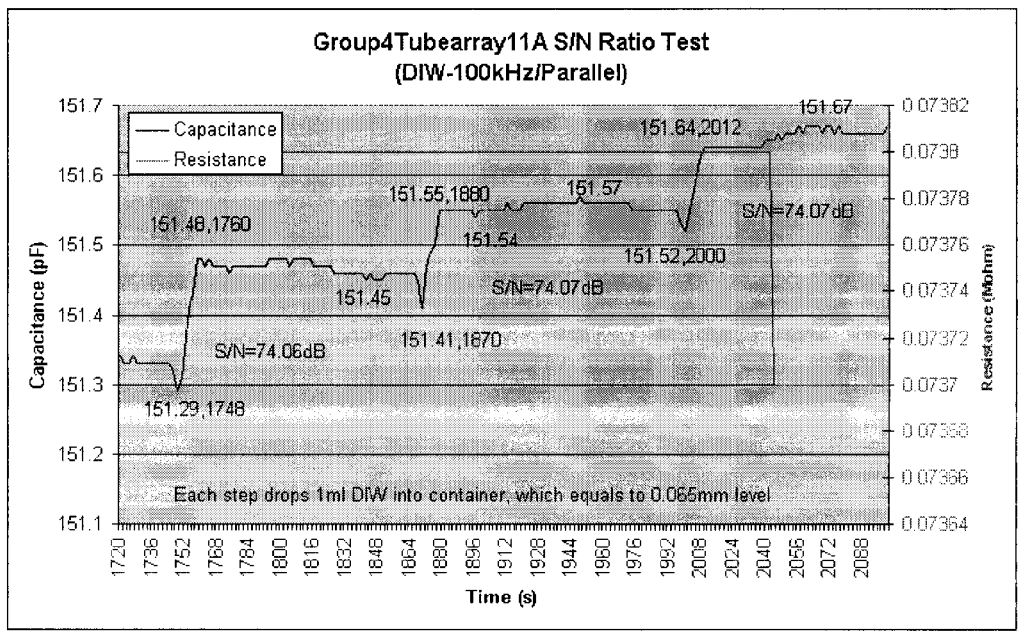
Fig. 16 Sensor S/N ratio test

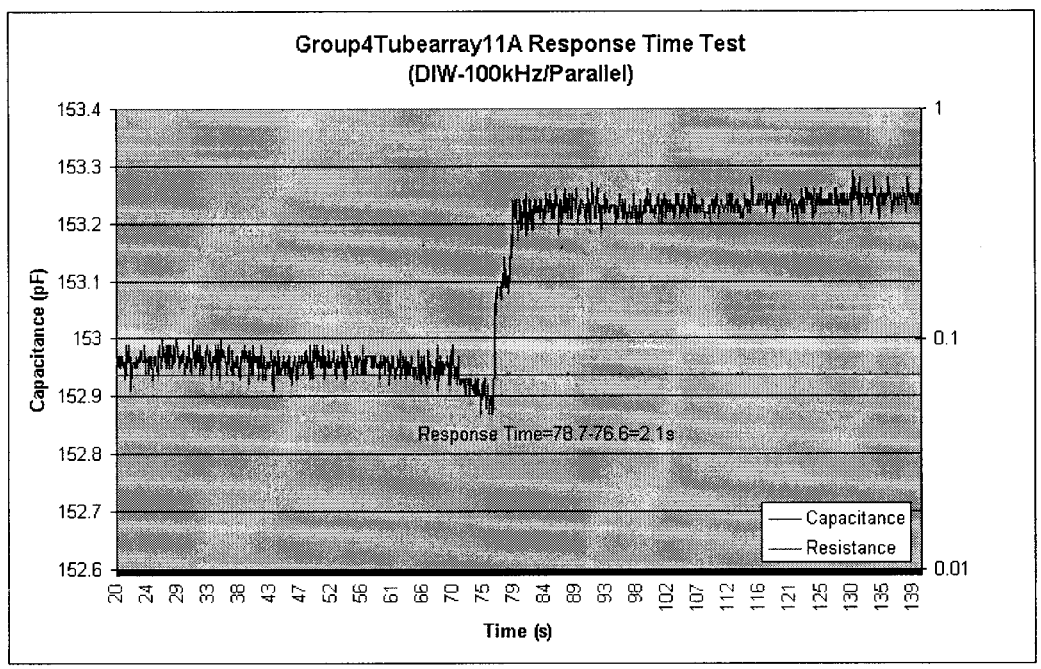
Fig. 17 Sensor response time test

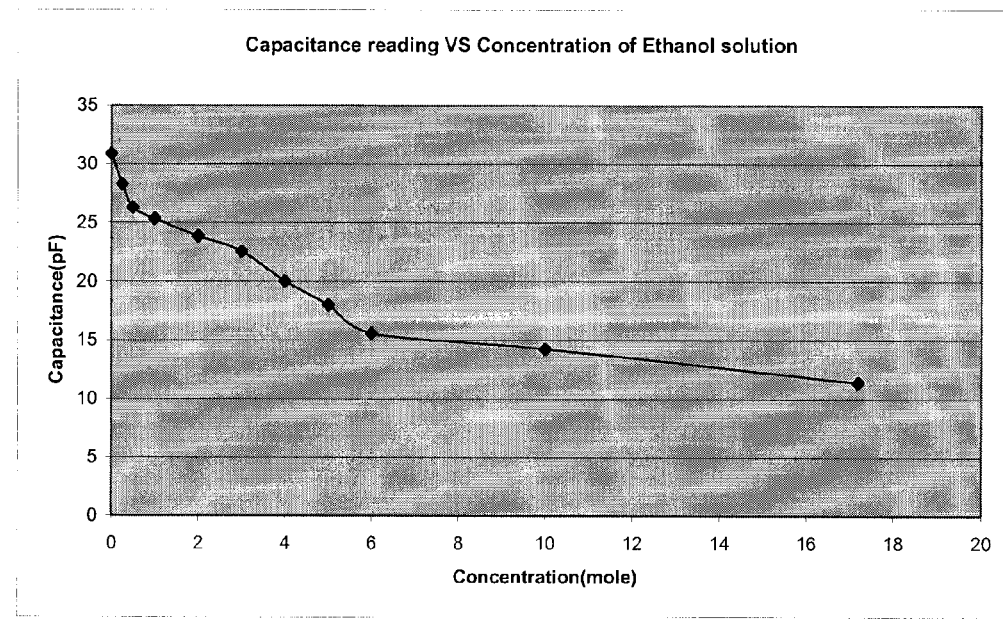
Fig. 18 Sensor test in ethanol solution
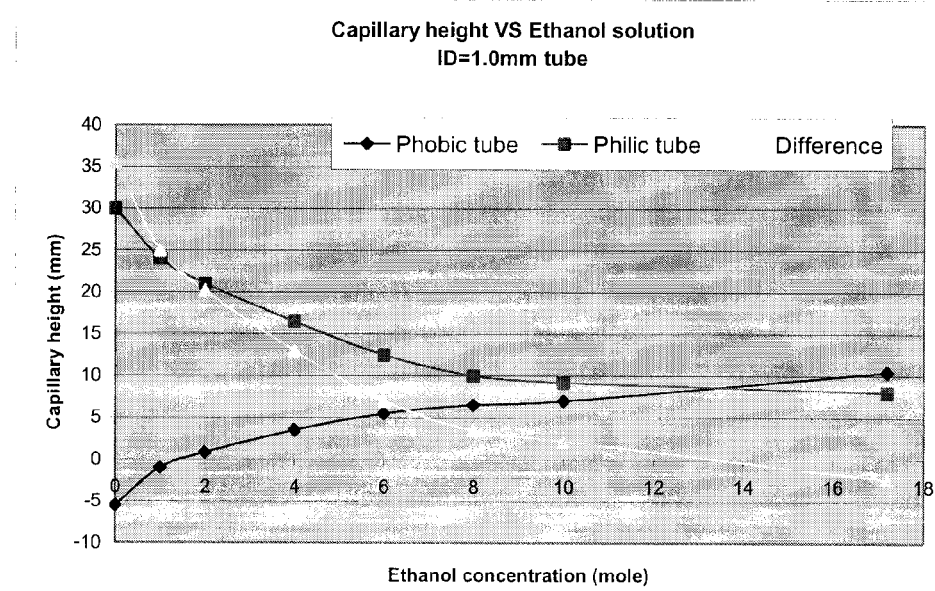
Fig. 19 Hydrophilic and hydrophobic tube capillary height in ethanol solution

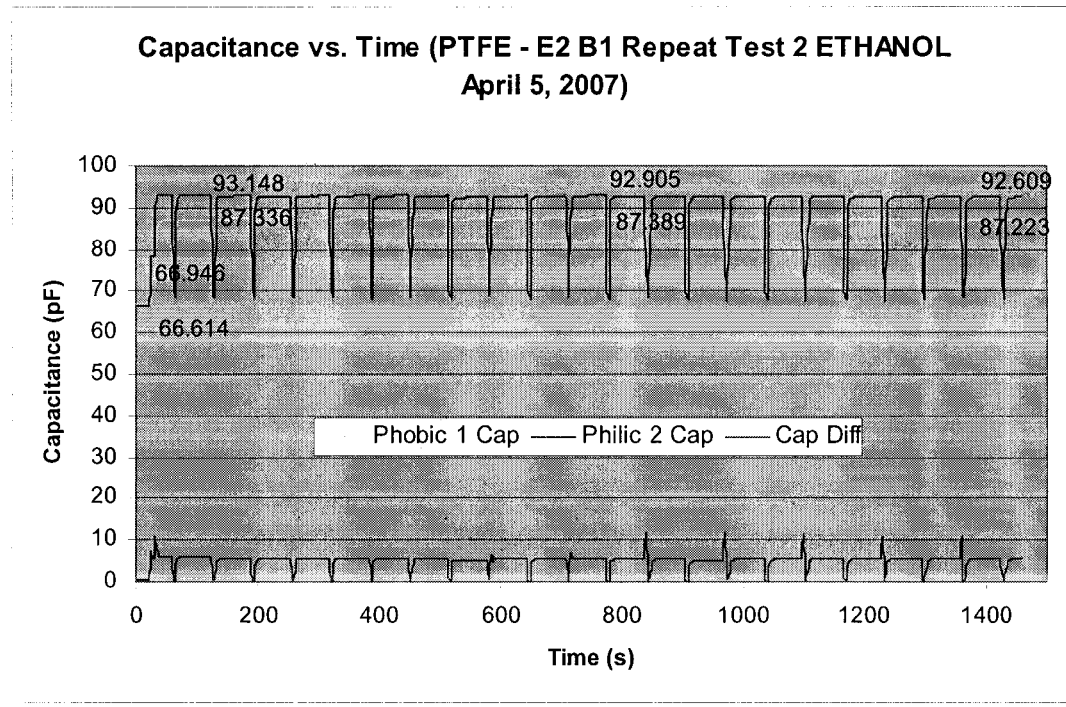
Fig. 20 Sensor repeatability test at one dipping in ethanol solution
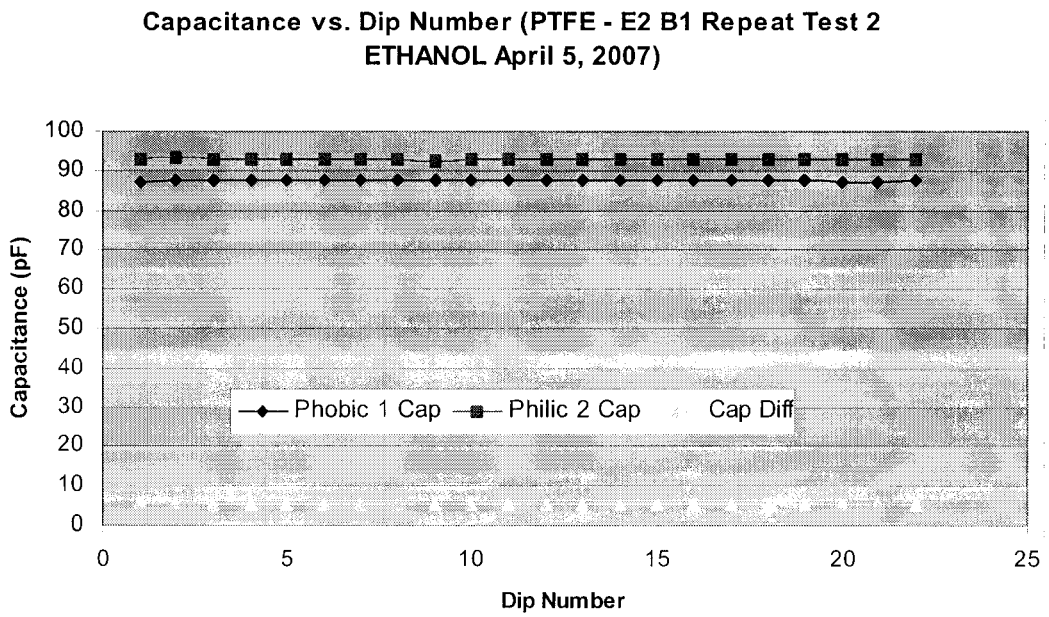
Fig. 21 Sensor repeatability test at different dipping in ethanol solution

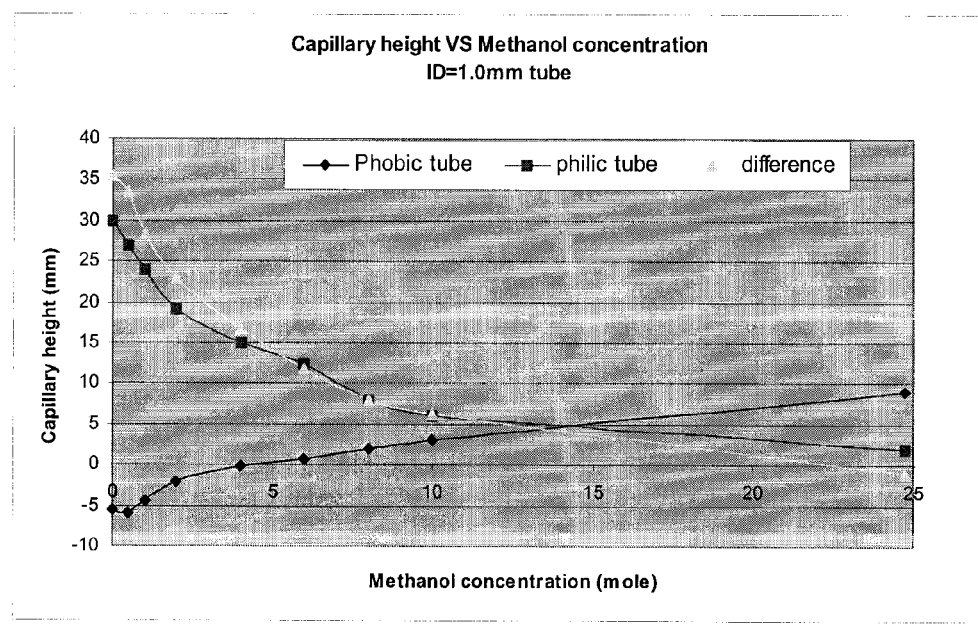
Fig. 22 Hydrophilic and hydrophobic tube capillary height in methanol solution

SENSOR FOR MEASURING THE CONCENTRATION OF A SOLVENT OR SOLUTE IN A MIXED SOLUTION SYSTEM

CROSS-REFERENCE TO RELATED APPLICATIONS

This application is a national phase entry of International Patent Application PCT/CA2010/000160 filed Feb. 5, 2010, which claims the benefit of U.S. Provisional Patent Application Ser. No. 61/202,209 filed Feb. 5, 2009.

BACKGROUND OF THE INVENTION

This invention relates to a sensor for measuring the concentration of a solute or a solvent in a mixed solution system, and in particular to a sensor for measuring the concentration of a low molecular weight alcohol, such as methanol and ethanol, particularly in an aqueous liquid feed solution for a fuel cell, e.g., a direct methanol fuel cell (DMFC), a direct ethanol fuel cell (DEFC), DMFC/DEFC test stations, and in aqueous solutions at ethanol/methanol refineries, alcohol production plants, chemical labs, and other systems where a solvent or solute concentration needs to be determined and monitored.

Liquid feed fuel cells operate directly on an organic liquid fuel stream, typically supplied as an aqueous fuel solution. Ethanol is used as the fuel, although methanol is predominantly used.

Direct methanol fuel cells/ethanol fuel cells have been the subject of considerable research during the last ten years. As a result, significant improvements in power density, efficiency, and lifetime have been reported. Performance levels achieved in cells, stacks, and systems show that this technology is a promising power source for a wide range of portable applications.

A direct methanol fuel cell (DMFC) is a type of solid polymer fuel cell that operates directly on a methanol fuel stream typically supplied as a methanol/water vapour or as an aqueous methanol solution in liquid feed DMFCs. The methanol in the fuel stream is directly oxidized at the anode therein. There is often a problem in DMFCs with crossover of methanol fuel from the anode to the cathode side through the membrane electrolyte. The methanol that crosses over typically then reacts with oxidant at the cathode and cannot be recovered, resulting in significant fuel inefficiency and deterioration in fuel cell performance. To reduce crossover, dilute solutions of methanol (for example, about 5 wt % methanol in water) are typically used as fuel streams in liquid feed DMFCs. The fuel streams in DMFCs are usually recirculated in order to remove carbon dioxide (a by-product of the reaction at the anode) and to re-use the diluent and any unreacted fuel in the depleted fuel stream exiting the DMFC. Methanol is added to the circulating fuel stream before it re-enters the fuel cell in order to compensate for the amount consumed, thereby providing a fresh mixture at the desired methanol concentration. Since the amount of methanol consumed is variable (depending on the load, crossover, and other operating parameters), the methanol concentration in the circulating fuel stream is usually measured continuously with a suitable sensor, and fresh methanol is admitted in accordance with the signal from the sensor. The concentration of methanol in the fuel circulation loop is an important operating parameter because it determines the electrical performance and efficiency of the direct methanol fuel cell system. The practical operation of direct methanol fuel cell systems requires accurate monitoring and control of methanol concentration, which is strongly dependent on a methanol concentration sensor.

A viable methanol concentration sensor should have a sensitivity of about ±0.02 M over the range of 0.1-2 M, with a response time of less than 1 s, although in general such specifications would be highly dependent on the mode of operation and the application. There are many factors to consider in developing a methanol sensor suitable for DMFCs. These factors include cost, size, simplicity, reliability, longevity, concentration range, and dynamic response. In particular, reliability and low cost should be addressed.

Methanol concentration sensors measure methanol concentration by means of detecting the variations of physical/chemical properties of the solution. Various types of sensors have been considered for the purposes of measuring the concentration of methanol in aqueous solution and thus for use in a recirculating fuel stream in a liquid feed DMFC.

1). Electrochemical-Based Sensors

An electrochemical-based sensor is a small DMFC, generally based on the electro-oxidation of methanol to carbon dioxide on platinum ruthenium catalysts [Barton, S. A. C., Muranch, B. L., Fuller, T. F., and West A. C., J. Electrochem. Soc. 1998, 145, 3783-3788; S. R. Narayanan, S. R., Valdez, T. I., and Chun, W., "Design and operation of an electrochemical methanol concentration sensor for direct methanol fuel cell,", Electrochemical and Solid-State Letters 2000, 3, 117-120; Qi, Z., He, C., Hollett, M., Attia, A., and Kaufman, A., "Reliable and fast-responding methanol concentration sensor with novel design," Electrochemical and Solid-State Letters 2003, 6, A88-A90; H. Zhao, J. Shen, J. Zhang, H. Wang, D. P. Wilkinson, C. E. Gu, Journal of Power Sources 2006, 159, 626-636].

By keeping the anode potential at a certain voltage (>0 V and ≤0.7V), the current produced by the sensor is proportional to the concentration of the methanol solution. Thus this type of sensor electrochemically measures the concentration of methanol aqueous solution used in a DMFC system. This type of sensor is probably the most popular one.

2). Electric-Capacitance Type Sensors

This type of sensor measures the change in dielectric constant of the fuel stream. The capacitance of a capacitor is measured with the methanol aqueous solution placed as a dielectric. The dielectric constant of the solution is proportional to the measured capacitance, and upon determining the dielectric constant of the solution, the methanol concentration in the mixture or in the electrolyte can be calculated [e.g. see US 2002/109511].

3). Infrared Sensing

This sensing technique uses an infrared sensor device for measuring methanol's content in water solutions in the fuel circulation loop of a DMFC [e.g. see U.S. Pat. No. 6,815, 682]. The infrared sensor is designed based on a specific methanol absorption peak in the infrared range. The IR spectrum of an aqueous solution of methanol shows a well-distinguished absorption peak at a wavelength of about 9.85 micrometers. The amplitude of the absorption peak is proportional to methanol concentration.

4). Ultrasound Sensing

The speed of sound in a water-methanol system increases significantly with methanol content; techniques for measuring characteristic sound velocities are used to measure methanol concentration [e.g. see U.S. Pat. No. 6,748,793].

5). Other Techniques

Other techniques include the measurement of viscosity or heat capacity or boiling temperature of methanol solution to determine the methanol concentration. There is one technique eliminating the need for a separate sensor by calculating the methanol concentration as a function of the observed current, the temperature of the fuel stream entering the DMFC stack, and the temperature of the DMFC stack itself [e.g. see U.S. Pat. No. 6,698,278]. Coulometric methods are really only accurate when there are no other $H_3OH$ losses (such as crossover, etc.).

Disadvantages and Limitations of the Prior Art Sensors

1). Electrochemical-based sensors suffer from degradation of the electrode reaction resulting in performance deterioration or failure over time.

2). Electric-capacitance type sensors measure the change in dielectric constant of the fuel stream. In theory, the larger the difference between the dielectric properties of two components of the fuel stream, the more precise the measurement can be. Unfortunately, the difference in dielectric constants for methanol-water systems is relatively small which may lead to misleading results or failure. For example, capacitance measurement has been used as a means of monitoring methanol concentration in a mixture of gasoline and methanol [e.g. see U.S. Pat. Nos. 4,939,467 and 5,196,801]. Due to the difference in dielectric constants between methanol and gasoline, the capacitance between two electrodes changes with the methanol concentration. Unfortunately, because the dielectric constant difference between water and methanol is much less than that between gasoline and methanol, and the methanol concentration used in a DMFC is normally less than 5 wt %, such a method can hardly provide a satisfactory measure of methanol concentration in water.

3). The infrared sensing has been proven effective for measuring the concentration of methanol in the range 0% to 5 wt % in water solution. For a wider range, this technique needs to be proven.

4). The ultrasound sensing system is not easy to miniaturized, and the cost is not low.

SUMMARY OF THE INVENTION

According to the present invention, an apparatus and method are provided for measuring the concentration of a low-molecular weight alcohol, such as methanol and ethanol in an aqueous solution thereof, as determined by measuring the change in capacitance of a capacitor (e.g. a cylindrical capacitor in the form of a small diameter capillary tube) dipped in and partially filled with the aqueous alcohol solution.

When the capillary tube is dipped into a methanol or ethanol aqueous solution, the capillary height of the solution in the capillary tube changes with the methanol/ethanol concentration of the solution because the surface tension of the solution varies with the concentration. The capacitance of the capacitor changes with the concentration of the solution because of the change of the capillary height and the change of the relative permittivity of the solution. The capacitor then can be a sensor to measure the solution concentration.

Since the depth of capillary tubes dipping in the solution affects the capacitance reading of the sensor, a second independent sensor can be provided as a reference sensor. The provision of the second/reference sensor eliminates the effect of depth of dipping of the first sensor, such that the difference in capacitance between the first and second sensors provides a concentration reading independent of the dipping depth.

According to one aspect of the invention, an apparatus is provided for measuring the concentration of a low molecular weight alcohol, in an aqueous liquid feed solution, comprising a hydrophilic capillary tube disposed between two electrodes to form a single hydrophilic sensor which acts as a capacitor, means for controlling the depth of dipping of the sensor in the aqueous solution, means for measuring the capacitance of the capacitor and control means including a computer, wherein the capacitance is a measure of the concentration of the solution.

In an embodiment of this aspect of the invention, the hydrophilic capillary tube is in the form of a layer of multiple hydrophilic capillary tubes.

According to another aspect of the invention, an apparatus is provided for measuring the concentration of a low molecular weight alcohol, in an aqueous liquid feed solution, comprising
a first sensor including a hydrophilic capillary tube having an inner diameter, being disposed between two electrodes to form a first capacitor,
a second sensor including a hydrophobic capillary tube having the same inner diameter as a capillary tube of the first sensor; said hydrophobic capillary tube having a hydrophobic coating on the inner diameter, being disposed between two electrodes to form a second capacitor, wherein the first hydrophilic and second hydrophobic sensors are dipped to the same depth in the aqueous solution to measure the solution concentration, means for measuring the capacitance of the two capacitors, and control means including a control circuit driven by a computer, wherein the difference in capacitance between the two capacitors is a measure of the concentration of the solution, independent of the depth of dipping of the two capacitors in the aqueous solution.

In an embodiment of this aspect of the invention, the first sensor comprises a layer of multiple hydrophilic capillary tubes queued between two coaxial cylindrical electrodes. Similarly, the second sensor comprises a layer of multiple hydrophobic capillary tubes queued between two coaxial cylindrical electrodes.

In another embodiment of this aspect of the invention, the first hydrophilic and second hydrophobic sensors are assembled together coaxially in a single cylinder, three coaxial cylindrical electrodes being provided, such that the hydrophilic capillary tubes are queued between the first and second co-axial cylindrical electrodes to form the first hydrophilic sensor, whilst the hydrophobic capillary tubes are queued between the second and third co-axial cylindrical electrodes to form the second/reference hydrophobic sensor.

In an embodiment of the invention, the means for measuring the capacitance includes a capacitance measurement circuit, applied to measure the capacitance between the two sensors, and the control means includes a control circuit, driven by a computer, for alternative measurement of the outputs of the first hydrophilic sensor and of the second hydrophobic sensor, respectively. The measured capacitance varies with the concentration because of change in the surface tension coefficient and relative permittivity with variation of the alcohol concentration.

In an embodiment of the invention, the hydrophobic coating is formed from materials such as silicon-containing compounds, including alkylchlorosilanes e.g. dimethyldichlorosilane, trimethylchlorosilane and cotadecyltrichlorosilane; fluoropolymers e.g. polytetrafluoroethylene, perfluoroalkoxy polymers and fluorinated ethylene propylene; and fluorinated elastomers, such as fluorinated hydrocarbons, fluoro silicone, acrylonitrile butadone and polyethylene wax.

According to another aspect of the invention, a method is provided for measuring the concentration of a low molecular weight alcohol, such as methanol and ethanol, in an aqueous liquid feed solution, comprising (a) providing an apparatus as described above, including a hydrophilic sensor (b) dipping the hydrophilic sensor in the aqueous solution and (c) measuring the capacitance of the sensor, wherein the capacitance is a measure of the concentration of the solution.

According to another aspect of the invention, a method is provided for measuring the concentration of a low molecular weight alcohol, such as methanol and ethanol, in an aqueous liquid feed solution, comprising (a) providing an apparatus as described above, including a first hydrophilic sensor and a second hydropobic sensor (b) dipping the first and second sensors in the aqueous solution and (c) measuring the capacitance of the two sensors, wherein the difference in capacitance of the two sensors is a measure of the concentration of the solution.

BRIEF DESCRIPTION OF THE DRAWING

FIG. 1 is a schematic illustration of hydrophilic and hydrophobic sensors, dipped in an aqueous solution of a low molecular weight alcohol, illustrating the different heights of solution in the capillary tubes.

FIG. 2 is a pictorial view of a hydrophilic single sensor according to the invention, partially cut away to illustrate the arrangement of a layer of multiple capillary tubes in cylindrical form.

FIG. 3 is a pictorial view of a hydrophilic single sensor according to the invention, illustrating the arrangement of a layer of multiple hydrophilic capillary tubes queued in between a pair of co-axial electrodes.

FIG. 4 is a pictorial view of sensing parts of a hydrophilic single sensor according to the invention, partially cut-away to illustrate its component parts.

FIG. 5 is a pictorial view of a hydrophilic single sensor according to the invention, partially cut-away to illustrate all of its component parts. A hydrophobic single sensor is built up in the same way as the hydrophilic one except replacing the hydrophilic capillary tubes with hydrophobic ones.

FIG. 6 is a pictorial view of the assembled sensors embodiment, partially cut-away to show a layer of multiple hydrophilic capillary tubes and a layer of multiple hydrophobic capillary tubes disposed concentrically in a circular fashion to create a cylindrical shape.

FIG. 7 is a schematic illustration of a capacitance measurement circuit used to measure the capacitance of the sensors according to the invention.

FIG. 8 is a schematic illustration of a computer controlled capacitance measurement control circuit according to the invention.

FIGS. 9 and 10 are graphs, illustrating the linearity performance of the hydrophilic and hydrophobic sensors, respectively.

FIGS. 11 and 12 are graphs, illustrating the accuracy of the hydrophilic and hydrophobic sensors, respectively.

FIGS. 13 to 22 are graphs illustrating various performance criteria of the sensors according to the invention.

DETAILED DESCRIPTION OF THE INVENTION

The sensor, apparatus and method according to the invention can be used to determine the concentration of a low molecular weight alcohol, such as methanol and ethanol, in an aqueous solution thereof, by measuring the change in capacitance of a capacitor (e.g. a cylindrical capacitor in the form of a small diameter capillary tube) dipped in and partially filled with the aqueous alcohol solution. When the first hydrophilic and second hydrophobic sensors are dipped into the solution to the same depth, the capillary tubes of both sensors are filled up to certain height levels, depending on the depth of dipping (FIG. 1).

H, is the solution height from the solution surface in the hydrophilic capillary tube (E), and h is the solution depth in the hydrophobic capillary tube (B) measured from the solution surface. H+h remains unchanged when both the hydrophilic and hydrophobic tubes are simultaneously dipped into the methanol/ethanol solution of a certain concentration (FIG. 1).

The capillary tube in the first hydrophilic sensor is unaltered and considered hydrophilic. The capillary tube in the second hydrophobic sensor is considered hydrophobic; the inner diameter of the said tube being coated with a hydrophobic material. The hydrophilic capillary tube is disposed between two electrodes to form the first hydrophilic sensor which acts as a first capacitor. The hydrophobic capillary tube is disposed between two electrodes to form the second hydrophobic sensor which acts as a second capacitor. The capacitance difference between the hydrophilic and hydrophobic sensors yields a concentration reading independent of sensor dipping depth.

The means for measuring the capacitance includes two parts, one part for measuring the capacitance of the sensors, e.g. a Stanford Research System Model SR720 LCR meter (capacitance measurement accuracy 0.05%). The other part is a control circuit driven by a computer for alternative measurement of the outputs of the first hydrophilic sensor and of the second hydrophobic sensor, respectively.

Two types of sensors were built: a hydrophilic sensor comprising a layer of multiple hydrophilic tubes (E) queued between a pair of coaxial cylindrical electrodes (see FIGS. 2-5), as well as a hydrophobic sensor comprising a layer of multiple hydrophobic tubes (B) queued between a pair of coaxial cylindrical electrodes. FIG. 1 shows a hydrophilic capillary tube (E) and a hydrophobic tube (B).

The following theoretical calculations can be used to estimate the capacitance deference of the hydrophilic and hydrophobic sensors.

Each sensor can be considered as a capacitor comprising two component capacitors connected in parallel: the one component capacitor has the solution as its dielectric (2), and the other has air as its dielectric (1) (FIG. 1). FIG. 1 shows the hydrophilic sensor acting as a capacitor comprising two component capacitors $C_{E1}$ and $C_{E2}$, and the hydrophobic sensor acting as a capacitor comprising two component capacitors $C_{B1}$ and $C_{B2}$.

Overall capacitances for hydrophobic and hydrophobic sensors ($C_E$ and $C_B$, respectively):

$$C_E = C_{E1} + C_{E2}$$

$$C_B = C_{B1} + C_{B2}$$

By ignoring the edge effect, the capacitances can be estimated as $$C_{E1}(\xi) = \frac{2\pi\varepsilon_0[L - H(\xi) - d(\xi)]}{\ln\left(\frac{b}{a}\right)}$$

$$C_{E2}(\xi) = \frac{2\pi\varepsilon_0\varepsilon_r(\xi)[H(\xi) + d(\xi)]}{\ln\left(\frac{b}{a}\right)}$$

$$C_{B1}(\xi) = \frac{2\pi\varepsilon_0[L - d(\xi) + h(\xi)]}{\ln\left(\frac{c}{b}\right)}$$

$$C_{B2}(\xi) = \frac{2\pi\varepsilon_0\varepsilon_r(\xi)[d(\xi) - h(\xi)]}{\ln\left(\dfrac{c}{b}\right)}$$

Here $\varepsilon_0$ and $\varepsilon_r$ are the permittivity of air and relative permittivity of the aqueous methanol/ethanol solution, respectively, and $\varepsilon_r$ changes with the methanol/ethanol concentration $\xi$. a and b (a<b) are the inner and outer radii of the two coaxial cylinder electrodes of the first sensor, respectively; b and c (b<c) are the inner/outer radii of the two coaxial cylinder electrodes of the second sensor, respectively. d is the depth of the tubes dipping in methanol/ethanol solution. L is the length of the capillary tube.

When the dipping depth can be controlled to remain unchanged, e.g. by providing control means therefore, e.g. by means of controlling the depth of dipping, such as conventional supporting frame and bracket arrangement or the like, the hydrophilic sensor can be used to measure the concentration of the solution (FIG. 1). $C_E = C_{E1} + C_{E2}$ can be employed to estimate the capacitance of the hydrophilic sensor.

When the dipping depth varies, the $C_E$ and $C_B$ both are varying not only with the concentration of the methanol/ethanol solution but also with the dipping depth of the sensors. Neither $C_E$ nor $C_B$ can be directly used to measure the concentration of the solution. Fortunately, the capacitance difference ΔC between $C_E$ and $C_B$ does not depend on the dipping depth and can be used to measure the concentration of the solution.

$$\Delta C = C_E - C_B$$
$$= (C_{E1} + C_{E2}) - (C_{B1} + C_{B2})$$

FIGS. 2 to 5 provide a pictorial view of a single hydrophilic sensor as an example. In this embodiment, the hydrophilic sensor is in the form of a layer of multiple hydrophilic capillary tubes co-axially aligned in a cylindrical configuration. A hydrophobic single sensor is built up in the same way as the hydrophilic one except replacing the hydrophilic capillary tubes with hydrophobic ones.

As can be seen from FIG. 5, the parts of the sensors are indicated by the following reference numerals.
1. EPDA "O" Seal ring
2. Silicon seal
3. PTFE bottom press ring
4. PTFE Sensor cap
5. Capillary glass tubes
6. Electrodes (Copper/stainless steel)
7. PTFE tight nut
8. PTFE up press ring
9. PTFE glass tube holder
10. Sensor base For the embodiment of the sensor wherein separate hydrophilic and hydrophobic sensing tubes are used, they are designed and machined separately in order to simplify the machining and assembly of the sensor prototypes.

In another embodiment, for practical applications, the size of the sensors can be miniaturized. Accordingly, the two types of sensors can be assembled together in a single coaxial cylinder, as shown in FIG. 6.

FIG. 6 provides a pictorial view of the embodiment of the apparatus, wherein the hydrophilic and hydrophobic sensors are each in the form of a layer of multiple capillary tubes, assembled together and coaxially aligned in a cylindrical configuration, to measure the solution concentration. The same principles of capillary action and capacitance principles apply. This embodiment is used to generate the following data.

The design involves a layer of multiple hydrophilic capillary tubes and a layer of multiple hydrophobic capillary tubes arranged concentrically and aligned in a circular fashion to create a cylindrical shape (FIG. 6).

Three co-axial cylindrical electrodes are provided, such that the hydrophilic capillary tubes are queued between the first and second co-axial cylindrical electrodes to form the first hydrophilic sensor, whilst the hydrophobic capillary tubes are queued between the second and third co-axial cylindrical electrodes to form the second/reference hydrophobic sensor. It will be appreciated by those skilled in the art that the inner layer of tubes can be hydrophilic and the outer layer of tubes hydrophobic, or vice versa.

These three electrodes form three-wire connection of the two capacitors. When the sensor is immersed in ethanol/methanol solution, the height of liquid in both types of tubes is determined by the surface tension, which depends on methanol/ethanol concentration. Also, the capacitance between each pair of electrodes will be associated with the relative permittivity of the liquid, which also depends on methanol/ethanol concentration.

It is important to note, however, that a change in concentration will not significantly alter the relative permittivity of the solution because of the fact that the difference of the relative permittivity between the water and ethanol/methanol is not very significant. It is the difference between the permittivity of air and the constant permittivity of the solution that causes a noticeable capacitance change. Since the permittivity of methanol/ethanol and water is greater than that of air, a higher capacitance occurs with a greater amount of solution present in the tubes. The predominant form of capacitance change is therefore caused by a change in surface tension.

Capacitance Measurement Circuit

Capacitance measurement circuit includes two parts, one (see FIG. 7) for measuring the capacitance of the sensors, e.g. using a SR720 meter to measure the capacitance. The other part is a control circuit (FIG. 8) driven by a computer to alternatively measure the outputs of the first hydrophilic sensor and of the second hydrophobic sensor, respectively, through the SR720.

Test Results

Methanol and ethanol solutions are very volatile, so all the linearity, repeatability, accuracy, resolution, signal-to-noise (S/N) ratio and response time tests are tested in DI water.

Capillary tube linearity working range determination (16 mm±6 mm, start from dipping depth of sensor 10 mm to 22 mm)

Due to capillary tube's length and hydrophobic/hydrophilic affection, both tubes (out Diameter OD=1.5 mm, inner Diameter ID=1.0 mm, 75 mm in length) have different linear working range when they dip into the methanol/ethanol solution. Table 1 shows testing result in DI water.

TABLE 1

Hydrophilic and hydrophobic tube linear working range

| Test# | Hydrophobic tube start range (mm) | Hydrophilic tube end range (mm) |
|---|---|---|
| 1 | 8 | 18 |
| 2 | 10 | 22 |

TABLE 1-continued

Hydrophilic and hydrophobic tube linear working range

| Test# | Hydrophobic tube start range (mm) | Hydrophilic tube end range (mm) |
|---|---|---|
| 3 | 10 | 20 |
| 4 | 8 | 22 |
| 5 | 10 | 28 |
| 6 | 12 | 24 |
| 7 | 10 | 22 |
| 8 | 10 | 24 |
|  | Average start range 9.75 mm | Average end range 22.5 mm |

Sensor Linearity Working Range (15 mm±5 mm, Start from Dipping Depth of the Sensor 10 mm to 20 mm)

For the first hydrophilic sensor (with hydrophilic tubes), the linearity working range starts at the sensor dipping into the solution and ends approximately at 20 mm depth of the sensor dipping in the solution. For the second hydrophobic sensor (with hydrophobic tubes), the linearity working range starts at around 10 mm depth of the sensor dipping in solution and lasts quite longer (>40 mm in depth), however, the overlapped linearity working range for both hydrophilic and hydrophobic sensors is about 10 mm, that is roughly from 10 mm to 20 mm in depth (see FIGS. 9 and 10).

For the first hydrophilic sensor, the linearity working range increases with increase of the length of the capillary tubes, so for further design, in order to increase the overlapped linearity working range for both the first and second sensors, the hydrophilic capillary tubes should be increased to approximately 100 mm in length so that overall linearity working range of both sensors can be extended to 30 mm in total, that is roughly from 10 mm to 40 mm in depth of the sensors in testing solutions.

Sensor Accuracy (Direct Measurement Error<3.89%, after Rectification<0.89%)

For both the hydrophilic and hydrophobic sensors, the capacitance reading increases with the depth of sensor dipping in solutions, but the slope of the capacitance increase is slightly different due to machine and assembly tolerances. This causes measurement error (3.89%), however, it can be rectified after sensors are assembled, and the accuracy of the sensor can be improved, measurement error can be reduced to 0.89% less than 1% (see FIGS. 11 and 12).

Note:
% E $C_1$-$C_2$—measurement error before rectification
% E CALC—measurement error after rectification

TABLE 2

Sensor accuracy test results at different working range (depth of sensor dipping is in the range from 10 to 18 mm)

| Range (mm) | Diff C1-C2 (pF) | Diff CALC (pF) | C1-C2 Avg (pF) | CALC Avg (pF) | ?/Avg C1-C2 (pF) | ?/Avg CALC (pF) | % E C1-C2 | % E CALC |
|---|---|---|---|---|---|---|---|---|
| 4 | 0.4835 | 0.2304 | 20.6901 | 27.8488 | 0.0234 | 0.0083 | 2.3368 | 0.8274 |
| 6 | 0.5514 | 0.2304 | 20.6027 | 27.8364 | 0.0268 | 0.0083 | 2.6761 | 0.8278 |
| 8 | 0.5514 | 0.5300 | 20.6003 | 27.9157 | 0.0268 | 0.0190 | 2.6764 | 0.8906 |

TABLE 3

Sensor accuracy test results at different working range (depth of sensor dipping 10-18 mm)

| Range (mm) | Diff C1-C2 (pF) | Diff CALC (pF) | C1-C2 Avg (pF) | CALC Avg (pF) | ?/Avg C1-C2 (pF) | ?/Avg CALC (pF) | % E C1-C2 | % E CALC |
|---|---|---|---|---|---|---|---|---|
| 4 | 0.4388 | 0.0186 | 16.9730 | 27.2328 | 0.0259 | 0.0007 | 2.5855 | 0.0684 |
| 6 | 0.5314 | 0.1332 | 16.8935 | 27.2633 | 0.0315 | 0.0049 | 3.1455 | 0.4885 |
| 8 | 0.6622 | 0.2236 | 16.8197 | 27.2998 | 0.0394 | 0.0082 | 3.8869 | 0.8190 |

Sensor Repeatability (<0.78%, Range<8 mm; <1.49%, Range<10 mm)

Repeatability was tested when sensors are at different depth of dipping in solutions, (see FIGS. 13 and 14). Dipping depth is in the range from 10 mm to 20 mm.

TABLE 4

Sensor repeatability test at different depth of dipping

| Range | ΔC1-C2 | AvgC1-C2 | Δ/AvgC1-C2 | % EC1-C2 |
|---|---|---|---|---|
| 1 | 0.1524 | 40.5338 | 0.0038 | 0.3760 |
| 2 | 0.2360 | 40.5871 | 0.0058 | 0.5812 |
| 3 | 0.2360 | 40.6077 | 0.0058 | 0.5812 |
| 4 | 0.2360 | 40.5985 | 0.0058 | 0.5813 |
| 5 | 0.2360 | 40.5985 | 0.0058 | 0.5813 |
| 6 | 0.2360 | 40.6083 | 0.0058 | 0.5812 |
| 7 | 0.3168 | 40.5752 | 0.0078 | 0.7808 |
| 8 | 0.3168 | 40.5752 | 0.0078 | 0.7808 |
| 9 | 0.6038 | 40.5145 | 0.0149 | 1.4903 |
| 10 | 0.6038 | 40.5099 | 0.0149 | 1.4905 |

Sensor Resolution (<0.01 Mole)

The resolution test was carried out by drop 1 ml solution that is equivalent to 0.065 mm solution level change into container (see FIG. 15), and then the sensor picks up capacitance change. Capillary height difference between DI Water and 1 mole ethanol/methanol solution is about 6 mm.

Let $\gamma$ represent the resolution of the sensor $$\text{Then } \gamma = \frac{1}{1/(6/0.065)} = 0.011 \text{ mole}$$

Sensor S/N Ratio (>70 dB)

The S/N ratio was tested by dropping 1 ml DI water that is equivalent to 0.065 mm solution level change into container, then the sensor picks up capacitance change. During the each step up, the capacitance reading still varies a little; we treated the variation as noise, see FIG. 16.

Then:

$$S/N = 20\log \text{ (average of the capacitance reading/capacitance variation)}$$
$$= 74 \text{ dB}$$

Sensor Response Time (<2.1 s)

Measuring the time of starting to squeeze the rubber ball to force the solution out of the sensor and then release the ball immediately tested sensor response time. (See FIG. 17)

Sensor Test Results in the Ethanol and Methanol Solutions

Ethanol and Methanol Solution Test

The sensor (an assembly of hydrophilic and hydrophobic sensors) output (Capacitance reading) monotonously decreases with the increase of the ethanol (methanol) solution concentration (Table 5, FIG. 18), so it can be used to measure the alcohol concentration. The difference between solution height in hydrophilic capillary tube and hydrophobic capillary tube monotonously decreases with increase of the ethanol (methanol) concentration (see FIGS. 19 and 22). It also can be seen that sensor's repeatability decreases with the increase of the ethanol concentration due to both hydrophilic and hydrophobic tube losing their hydrophilic and hydrophobic strength with the solution surface tension change (see Table 6). That's why we can see the relative repeat error drops from 0.8% (Di water) to 8.4% (pure ethanol) (see FIGS. 20 and 21).

TABLE 5

Sensor test results in ethanol solution

| Ethanol (mole) | 0.25 | 0.5 | 1.0 | 2.0 | 3.0 | 4.0 | 5.0 | 6.0 | 10.0 | Pure17.2 | DIW |
|---|---|---|---|---|---|---|---|---|---|---|---|
| C1-C2 (pF) | 28.25 | 26.29 | 25.31 | 23.86 | 22.54 | 20.02 | 18.98 | 15.59 | 14.26 | 11.39 | 30.87 |

TABLE 6

Sensor repeatability test at different depth of dipping

| Range (mm) | ΔC1-C2 (pF) | C1-C2 Avg (pF) | Δ/Avg C1-C2 (pF) | % E C1-C2 |
|---|---|---|---|---|
| 1 | 0.1417 | 5.4112 | 0.0262 | 2.6180 |
| 2 | 0.1847 | 5.4344 | 0.0340 | 3.3981 |
| 3 | 0.1847 | 5.4439 | 0.0339 | 3.3922 |

TABLE 6-continued

Sensor repeatability test at different depth of dipping

| Range (mm) | ΔC1-C2 (pF) | C1-C2 Avg (pF) | Δ/Avg C1-C2 (pF) | % E C1-C2 |
|---|---|---|---|---|
| 4 | 0.1847 | 5.4461 | 0.0339 | 3.3908 |
| 5 | 0.4490 | 5.3902 | 0.0833 | 8.3299 |
| 6 | 0.4490 | 5.3934 | 0.0833 | 8.3250 |
| 7 | 0.4490 | 5.3955 | 0.0832 | 8.3217 |
| 8 | 0.4520 | 5.4067 | 0.0836 | 8.3600 |
| 9 | 0.4520 | 5.4031 | 0.0837 | 8.3656 |
| 10 | 0.4520 | 5.4007 | 0.0837 | 8.3693 |

5 tests at each depth have been conducted.

Following specifications of the assembled sensor are based on:
Sensor dimension: 025 mm×85 mm
Capillary tube OD=1.5 mm, ID=1.0 mm
Tubes in sensor coated with hydrophobic material, e.g. fluoropolymer 1. Sensor can be used to measure the concentration of ethanol solution in the range from 0 to 17 M.
2. Sensor can be used to measure the concentration of methanol solution in the range from 0 to 25 M.
3. Sensor specifications:
   Measurement range: 0~17 M (ethanol)
   0~25 M (methanol)
   Sensor dipping range: 15 mm±5 mm (10 mm)
   Accuracy: <1%
   Resolution: >0.01 mole
   S/N ratio: >70 dB
   Repeatability: <0.78% (<8 mm)
   Response time: <2.1 S

The invention claimed is:

1. An apparatus for measuring the concentration of a low molecular weight alcohol, in an aqueous liquid feed solution, comprising A hydrophilic sensor including a hydrophilic capillary tube being disposed between a first and second co-axial cylinder electrodes to form a first capacitor, a hydrophobic sensor including a hydrophobic capillary tube; said hydrophobic capillary tube having a hydrophobic coating on the its inner diameter, being disposed between the second and a third co-axial cylinder electrodes to form a second capacitor, wherein the hydrophilic and hydrophobic sensors are dipped to the same depth in the aqueous solution to measure the solution concentration, means for measuring the capacitance of the two capacitors, and control means including a control circuit driven by a computer, wherein the difference in capacitance between the two capacitors is a measure of the concentration of the solution, independent of the depth of dipping of the two capacitors in the aqueous solution, wherein the hydrophilic sensor comprises a layer of multiple hydrophilic capillary tubes queued between the first and second co-axial cylinder electrodes, and the hydrophobic sensor comprises a layer of multiple hydrophobic capillary tubes queued between the second and the third co-axial cylindrical electrodes, the layers of capillary tubes being disposed concentrically in circular fashion to create a cylindrical shape.

2. An apparatus according to claim 1, wherein the hydrophilic and hydrophobic sensors are assembled together co-axially in a single cylinder, such that the hydrophilic capillary tubes are queued between the first and second co-axial cylindrical electrodes to form the hydrophilic sensor, whilst the hydrophobic capillary tubes are queued between the second and third co-axial cylindrical electrodes to form the hydrophobic sensor.

3. An apparatus according to claim 2, wherein the means for measuring the capacitance includes a capacitance measurement circuit, applied to measure the difference in capacitance between the hydrophilic and hydrophobic sensors.

4. An apparatus according to claim 3, wherein the control means includes a control circuit driven by a computer, for alternative measurement of the outputs of the hydrophilic sensor and hydrophobic sensor, respectively.

5. An apparatus according to claim 4, wherein the hydrophobic coating is provided in varying strengths and selected from the group consisting of: silicon-containing compounds, fluoropolymers, and fluorinated elastomers.

6. An apparatus according to claim 5, wherein the low molecular weight alcohol is methanol or ethanol.

7. An apparatus according to claim 6, wherein a working depth of dipping range for the hydrophilic and hydrophobic sensors is 10 to 40 mm, provided by a tube length of 100 mm.

8. An apparatus according to claim 5, wherein the silicon containing compound is an alkylchlorosilane compound.

9. An apparatus according to claim 8, wherein the alkylchlorosilane compound is selected from the group consisting of: dimethyldichlorosilane, trimethylchlorosilane and cotadecyltrichlorosilane.

10. An apparatus according to claim 5, wherein the fluoropolymer is selected from the group consisting of: polytetrafluoroethylene, perfluoroalkoxy polymers and fluorinated ethylene propylene.

11. An apparatus according to claim 5, wherein the fluorinated elastomer is selected from the group consisting of: fluorinated hydrocarbons, fluoro silicone, acrylonitrile butadone and polyethylene wax.

12. A method for measuring the concentration of a low molecular weight alcohol, in an aqueous liquid feed solution, comprising:
    (a) providing an apparatus as described in claim 1,
    (b) dipping the hydrophilic and hydrophobic sensors in the aqueous solution, and
    (c) measuring the capacitance of the two sensors, wherein the difference in capacitance of the two sensors is a measure of the concentration of the solution.

13. A method according to claim 12, wherein the hydrophobic coating is selected from the group consisting of silicon-containing compounds, fluoropolymers, and fluorinated elastomers.

14. A method according to claim 13, wherein the low molecular weight alcohol is methanol or ethanol.

15. A method according to claim 14, wherein a working depth of dipping range for the hydrophilic and hydrophobic sensors is 10 to 40 mm, provided by a tube length of 100 mm.

16. A method according to claim 13, wherein the silicon-containing compound is an alkylchlorosilane compound.

17. A method according to claim 16, wherein the alkylchlorosilane compound is selected from the group consisting of: dimethyldichlorosilane, trimethylchlorosilane and cotadecyltrichlorosilane.

18. A method according to claim 13, wherein the fluoropolymer is selected from the group consisting of: polytetrafluoroethylene, perfluoroalkoxy polymers and fluorinated ethylene propylene.

19. A method according to claim 13, wherein the fluorinated elastomer is selected from the group consisting of: fluorinated hydrocarbons, fluoro silicone, acrylonitrile butadone and polyethylene wax.

\* \* \* \* \*